(12) United States Patent
Hu et al.

(10) Patent No.: US 11,773,072 B2
(45) Date of Patent: Oct. 3, 2023

(54) METHOD AND SYSTEM FOR PRODUCING EPOXYALKANE (71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Song Hu, Shanghai (CN); Shuai Hu, Shanghai (CN); Weisheng Yang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 253 days.

(21) Appl. No.: 16/768,663

(22) PCT Filed: Nov. 30, 2018

(86) PCT No.: PCT/CN2018/118519
§ 371 (c)(1),
(2) Date: May 30, 2020

(87) PCT Pub. No.: WO2019/105453
PCT Pub. Date: Jun. 6, 2019

(65) Prior Publication Data
US 2021/0171484 A1    Jun. 10, 2021

(30) Foreign Application Priority Data

Nov. 30, 2017 (CN) .......................... 201711239603.7
Nov. 30, 2017 (CN) .......................... 201711241136.1
Nov. 30, 2017 (CN) .......................... 201711241161.X (51) Int. Cl.
*B01D 3/40*   (2006.01)
*C07D 301/32* (2006.01)
(Continued)

(52) U.S. Cl.
CPC .......... *C07D 301/32* (2013.01); *B01D 3/322* (2013.01); *B01D 3/324* (2013.01); *B01D 3/40* (2013.01); *C07D 303/04* (2013.01)

(58) Field of Classification Search
CPC .............................. B01D 3/40; C07D 301/32
See application file for complete search history.

(56) References Cited

U.S. PATENT DOCUMENTS 4,304,639 A * 12/1981 Hardy .................. C07D 301/32
                                                       203/DIG. 19
4,402,794 A    9/1983 Nemet-Mavrodin et al.
(Continued)

FOREIGN PATENT DOCUMENTS

CN      1633424 A     6/2005
CN      1678600 A     10/2005
(Continued)

OTHER PUBLICATIONS

Górak, Andrzej Sorensen, Eva. (2014). Distillation: Fundamentals and Principles—4.5.8 Reboilers and Condensers. (pp. 178). Elsevier. Retrieved from https://app.knovel.com/hotlink/pdf/id:kt00U6Z072/distillation-fundamentals/reboilers-condensers.*

(Continued)

*Primary Examiner* — Jonathan Luke Pilcher
(74) *Attorney, Agent, or Firm* — NKL Law; Allen Xue (57) ABSTRACT

A method for producing an epoxyalkane includes the step of separating a stream containing an epoxyalkane and an extracting agent in a separation column having a column (Continued)

kettle reboiler. A part of a stream in the column kettle of the separation column enters an extracting agent purifier and is treated to obtain a gas phase light fraction that returns to the separation column and a liquid phase heavy fraction that is subjected to a post-treatment. The method can be used in the industrial production of an epoxyalkane.

14 Claims, 2 Drawing Sheets

(51) Int. Cl.
  *C07C 303/04* (2006.01)
  *B01D 3/32* (2006.01)
  *C07D 303/04* (2006.01)

(56) References Cited

U.S. PATENT DOCUMENTS

| | | | |
|---|---|---|---|
| 4,772,732 A | 9/1988 | Huang et al. | |
| 4,875,909 A * | 10/1989 | Kakimoto | C07D 301/32 95/194 |
| 5,772,854 A * | 6/1998 | Nelson | C07D 301/32 203/64 |
| 9,278,945 B2 * | 3/2016 | Derking | B01D 3/40 |
| 2015/0158835 A1 | 6/2015 | Derking et al. | |

FOREIGN PATENT DOCUMENTS

| | | |
|---|---|---|
| CN | 1307168 C | 3/2007 |
| CN | 101006067 A | 7/2007 |
| CN | 104109137 A | 10/2014 |
| CN | 103977592 B | 1/2016 |
| CN | 105585543 A | 5/2016 |
| CN | 105669599 A | 6/2016 |
| CN | 106397361 A | 2/2017 |
| CN | 106397365 A | 2/2017 |
| CN | 108017598 A | 5/2018 |
| JP | S5646874 B2 | 4/1981 |
| JP | S59024982 B2 | 2/1984 |

OTHER PUBLICATIONS

Espacenet English language translation of CN 103977592.*
Espacenet English Translation of CN 103977592; Jan. 13, 2016 (publication date of patent document to which this translation corresponds) (Year: 2016).*

* cited by examiner

Fig. 1

PRIOR ART

Fig. 2

METHOD AND SYSTEM FOR PRODUCING EPOXYALKANE

FIELD OF THE INVENTION

The invention relates to a method for producing epoxyalkane and a system for producing epoxyalkane.

BACKGROUND OF THE INVENTION

Propylene oxide (PO) is mainly used for the production of polyether polyols, propylene glycol and propylene glycol ether and its output ranks only second to polypropylene among the propylene derivatives, thus it is the propylene derivative with the second largest output. According to statistics, the propylene oxide used for the worldwide production of polyether polyols in 2011 accounted for about 66% of the total consumption, the propylene oxide used for the worldwide production of propylene glycol made up about 17% of the total consumption, the propylene oxide used for the worldwide production of propylene glycol ether accounted for about 6% of the total consumption. The global propylene oxide production capacity in 2011 was 8.822 million tons, the production capacity exceeded 10 million tons in 2016. It is expected that the production capacity of propylene oxide will reach 12 million tons/year by 2020, and the quantity demand will reach 10 million tons/year. The market prospect of propylene oxide in the world is still optimistic in the long run.

1,2-butylene oxide (BO) is a homologue with ethylene oxide (EO) and propylene oxide (PO), and its molecular formula is $C_4H_8O$ (CAS number: 106-88-7). It is a substance having a three-membered ring structure and active chemical properties, and is mainly used as intermediates for polyether polyol monomers and other synthetic materials. 1,2-epoxybutane can also be used for producing foam plastics, synthetic rubbers, non-ionic surfactants and the like. It can replace acetone as a diluent for nitro paint, and may be further applied as a standard substance for chromatographic analysis.

The epoxyalkane products have strict requirements on the contents of water, aldehydes and isomers impurities. Water will affect the hydroxyl value and foaming properties of polymers. Aldehydes will cause the product to emit odors and affect people's health. The isomers are end-capping reagent for polymerized long-chains.

Therefore, the national standards and enterprise standards in China impose strict requirements on the product purity.

As stipulated in the Chinese national standard, the quality and purity requirements of the superior product of propylene oxide are as follows: the content of propylene oxide ≥99.95%, the content of water ≤0.02%, the content of acetaldehyde+propyl aldehyde ≤0.005%, and the content of acid ≤0.003%.

According to the BASF enterprise standards, the quality and purity requirements of the qualified product of 1,2-butylene oxide are as follows: the content of butylene oxide ≥99.5%, the content of butylene oxide isomers ≤0.2%, the content of total aldehydes ≤0.05%, and the content of water ≤0.03%.

The quality and purity requirements of the superior product of 1,2-butylene oxide are as follows: the content of butylene oxide ≥99.9%, the content of butylene oxide isomers ≤0.1%, the content of total aldehydes ≤0.015%, and the content of water ≤0.005%.

The crude epoxyalkane produced by the reaction usually contains impurities such as water, methanol, acetone and methyl formate; because these impurities form an azeotrope with the epoxyalkane or the relative volatility is close to 1, it is difficult to reach the epoxyalkane product standards through the ordinary distillation process.

The purification of epoxyalkane generally uses C7-C20 straight and branched chain hydrocarbons and/or diols as the extractant. For economic reasons, the purification process of epoxyalkanes uses a mixture of C8 straight and branched chain alkanes as the extractant. An addition of the extractant makes the relative volatility of acetaldehyde, water, methanol and methyl formate in regard to epoxyalkane to become larger, the acetaldehyde, water, methanol, and methyl formate are removed from the top of the column, and the extractant is recycled.

Given that the crude butylene oxide contains water and methanol, and water is added during the separation process, the following reactions occur during the purification of butylene oxide:

The 1,2-butylene oxide is hydrolyzed to form 1,2-butanediol, and the solubility of 1,2-butanediol in water is less than 1,2-butylene oxide.

1,2-butylene oxide reacts with methanol to form 1-butanediol monomethyl ether (ether bond is formed on the carbon atom of the terminal epoxy group), 2-butanediol monomethyl ether (ether bond is formed on the carbon atom of the 2-position epoxy group). In addition, both 1-butanediol monomethyl ether and 2-butanediol monomethyl ether are slightly soluble in water.

1,2-butylene oxide may subject to polymerization reaction to form polymers, such as dimeric butylene oxide and polybutylene oxide.

1,2-butylene oxide is reacted with active hydrogen-containing compounds such as water, dihydric alcohol or polyhydric alcohol to form poly-1,2-butanediol ether and derivatives thereof. The poly-1,2-butanediol ether and derivatives thereof are non-volatile viscous liquids, colorless to brown, and mostly soluble in ketones, alcohols, esters, hydrocarbons and halogenated hydrocarbons; the poly-1,2-butanediol ether and derivatives thereof having lower molecular weight are soluble in water, the water solubility decreases along with an increased molecular weight and the raised temperature.

Most of the above-mentioned reaction by-products and derivatives are hardly soluble in water and cannot be removed by water washing. When an extractive distillation method is used for refining the butylene oxide, the by-products and derivatives will accumulate in the extractant, thereby reducing the extraction efficiency of the extractant. Therefore, it is necessary to reduce the concentration of the by-products and derivatives in the extractant.

For example, the patent document U.S. Pat. No. 4,402,794 discloses the use of hydrocarbons having 7-9 carbon atoms, preferably N-octane as the extractant for a single extractive rectification to separate water, methanol, acetone, methyl formate and other impurities contained in the crude 1,2-butylene oxide solution. However, it does not involve with separation of impurity aldehydes. The organic layer layered by the phase separator at the top of the extractive distillation column is delivered to the rectifying column for distillation and separation of methanol, acetone and the like; the column kettle stream from the extractive distillation column is sent to the extractive rectifying column; a part of the column kettle liquid from the extractive rectifying column is discharged. In this method, a part of the column kettle liquid containing the extractant and heavy component is discharged to alleviate accumulation of the reaction by-products and derivatives in the extractant. Due to the low content of heavy component in the discharge stream of the column kettle, a large amount of extractant must be discharged in order to ensure purity of the extractant, thus a large amount of extractant will be lost.

As another example, the patent document U.S. Pat. No. 4,772,732 discloses a method for purifying butylene oxide by using an anion exchange resin and an adsorbent. The anion exchange resin removes acid and dehydrogen impurities while the adsorbent removes water from the impurities of butylene oxide. Depending upon the impurity level, the purification steps can be conducted singularly or in combination, and the process can proceed either batchwise in a reactor or continuously in a tower or column. The ion exchange resin of the choice is a sulfonated macroreticular anion exchange resin and the adsorbent of choice is a molecular sieve. The method is costly, the adsorption and desorption process is also complicated, and the processing capacity is not large.

Similarly, propylene oxide is hydrolyzed to produce 1,2-propylene glycol in a propylene oxide system. The solubility of 1,2-propylene glycol in water is less than propylene oxide. The reaction of propylene oxide with methanol produces propylene glycol monomethyl ether. Polymerization of propylene oxide will form polymers, such as dimeric propylene oxide and polypropylene oxide.

Propylene oxide reacts with compounds containing active hydrogen such as water, diols or polyols to form polypropylene glycol ethers and derivatives thereof. The solubility of polypropylene glycol ethers and derivatives thereof in both water and the organic phase is not large.

In summary, the current status of the prior art is that there is an urgent need for an epoxyalkane production method with small loss of extractant, high purity of the circulating extractant, high yield of epoxyalkane and low energy consumption.

SUMMARY OF THE INVENTION

A purpose of the present disclosure is to overcome the aforementioned defects of the prior art, and provide an epoxyalkane production method with small loss of extractant, high yield of epoxyalkane and low energy consumption.

Specifically, a first aspect of the present disclosure relates to a method for producing an epoxyalkane, the method comprises the following steps:
1) rectifying the stream containing epoxyalkane, extractant and heavy components such as diols and alcohol ether in a separation column, obtaining the stream mainly containing epoxyalkane from the column top, and obtaining the stream mainly containing extractant from the column kettle;
2) dividing the stream mainly containing extractant obtained from the column kettle into at least three streams, wherein the first stream is heated by the column kettle reboiler and returned to the separation column from the column kettle; the second stream is used as the circulating extractant; the third stream is delivered to an extractant purifier for carrying out purification treatment to remove heavy component whose boiling point is higher than that of the extractant, and obtain the vapor phase or vapor-liquid mixture treated as light components which is mainly extractant;
3) returning the vapor phase or vapor-liquid mixture treated as the light components which are mainly extractant to the separation column.

A second aspect of the present disclosure provides another method for producing an epoxyalkane, the method comprises:
1) sending the crude product stream containing the epoxyalkane, the extractant, and the heavy components such as diols and alcohol ether to an extractive rectification column for performing extractive distillation, obtaining a stream including epoxyalkane, extractant, and heavy components such as diols and alcohol ether from the column kettle, wherein the diols and alcohol ether contain those brought in by the crude product stream containing epoxyalkane and those generated by the chemical reaction occurs during separation process of the extractive rectification column;
2) subjecting the stream including epoxyalkane, extractant, and heavy components such as diol and alcohol ether to rectification and separation in the separation column, obtaining the stream mainly containing epoxyalkane from the column top, and obtaining the stream mainly containing extractant from the column kettle;
3) dividing the stream mainly containing extractant from the column kettle into at least three streams, wherein the first stream is heated by the column kettle reboiler and returned to the separation column from the column kettle; the second stream used as the circulating extractant is conducted into the extractive rectification column; the third stream is delivered to an extractant purifier for carrying out purification treatment to remove heavy components such as diols and alcohol ether whose boiling point is higher than that of the extractant, and obtaining the vapor phase or vapor-liquid mixture treated as light component which is mainly extractant; 4) returning the vapor phase or vapor-liquid mixture treated as the light component which is mainly extractant to the separation column.

A third aspect of the present disclosure provides an epoxyalkane production system, the system comprises:
1) a separation column, wherein the column kettle having an outlet being capable of leading the column kettle stream out of the separation column;
2) a column kettle reboiler which is arranged at the lower part of the separation column to reboil part of the column kettle materials of the separation column, and return the reboiled column kettle material to the separation column;

3) an extractant purifier which is arranged underneath the feed position of the separation column for purifying a part of the column kettle material of the separation column to remove heavy components whose boiling point is higher than that of the extractant; obtaining the vapor phase or vapor-liquid mixture treated as light component which is mainly an extractant and returning the light component to the separation column.

A fourth aspect of the present disclosure provides another epoxyalkane production system, the system comprises:

1) an extractive rectification column for performing extractive rectification of crude product stream containing epoxyalkane;
2) a separation column for separating the column kettle stream from the extractive rectification column, obtaining the stream mainly containing epoxyalkane from the column top, and obtaining the stream mainly containing extractant from the column kettle;
3) a column kettle reboiler which is arranged at the lower part of the separation column to reboil part of the column kettle materials of the separation column, and return the reboiled column kettle material to the separation column;
4) an extractant purifier which is arranged underneath the feed position of the separation column for receiving and purifying a part of the column kettle material of the separation column to remove heavy components whose boiling point is higher than that of the extractant; obtaining the vapor phase or vapor-liquid mixture treated as light component which is mainly an extractant and returning the light component to the separation column.

The foregoing epoxyalkane production method provided by the present disclosure has the following specific favorable effects:

The present disclosure discloses a solution of adding an extractant purifier at the bottom of the existing separation column, introducing a part of the column kettle stream of the separation column that was originally directly discharged for recycling into the extractant purifier for performing treatment, removing impurities which are mainly diols and alcohol ethers from the liquid phase heavy components and returning the purified heavy components to the separation column, thereby improving purity of the extractant, decreasing replenishment amount of the extractant and reducing the discharge amount of waste liquid. Compared with the method of periodically discharging the extractant and uniformly processing impurities in the extractant in the prior art after the content of impurity in the extractant reaches a certain level, the present disclosure may reduce loss of the extractant and improve yield of the epoxyalkane. More specifically, the purity of extractant is increased by 0.1-2%, the loss of extractant only accounts for 0.01-0.1%, and the yield of epoxyalkane is increased by 0.5-5%.

In addition, the foregoing epoxyalkane production method provided by the present disclosure can also save energy consumption. Specifically, the foregoing epoxyalkane production method provided by the present disclosure reduces energy consumption by 1-10%. The present disclosure adopts the above-mentioned "breaking up the whole into parts" extractant purification mode, it only needs to add an extractant purifier, preferably a kettle-type reboiler on the basis of the existing device, it makes small change to the existing device, occupies a small area and requires a small investment, the favorable effects are very obvious and have an excellent industrial application prospect.

BRIEF DESCRIPTION OF THE DRAWINGS

In the drawings, the same components are represented with the same reference signs. The drawings are not necessarily illustrated according to the actual scale.

DESCRIPTION OF THE REFERENCE SIGNS

1. Feed stream
2. Extractant stream
3. Epoxyalkane product stream
4. Column kettle reboiler feed stream
5. Column kettle reboiler discharge stream
6. Extractant purifier feed stream
7. Heavy component impurity stream-effluent stream
8. Extractant purifier discharge stream
31. 1,2-butylene oxide product stream
A. Column kettle reboiler
B. Extractant purifier
C. Separation column

DETAILED DESCRIPTION OF THE PREFERRED EMBODIMENTS

The entirety of publications, patent applications, patents and other reference literatures mentioned in the description is hereby incorporated by reference herein. Unless otherwise defined, each of the technologies and scientific terminologies used in the description has meanings as commonly understood by those skilled in the art. In case of conflict, the definitions in the description shall prevail.

When the description uses the prefix "well-known among those skilled in the art", "prior art" or similar terms to define materials, substances, methods, steps, devices or components, the objects defined by the prefix cover those routinely used in the technical field when the invention is presented, but also cover those which are not commonly used at present and will become generally recognized in the art for being suitable for the similar purposes.

Apart from the content which is explicitly stated in the context of the description, any matter or item not mentioned herein is directly applied to those well-known in the art without a need of making any change. Moreover, any embodiment described herein can be freely combined with one or more other embodiments described herein, any of the thereby formed technical solutions or ideas shall be regarded as a part of the original disclosure or original record of the present invention, instead of being considered as the new content which has not been disclosed or anticipated herein, unless those skilled in the art believe that the combination is obviously unreasonable.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to yield one or more new numerical ranges, which should be considered as specifically disclosed herein.

Unless explicitly stated in the present disclosure, the expressions "first", "second" and "third" do not represent the order of priority, they are only used for the distinguishing purpose, for example, the expressions "first", "second" and "third" in the terms "first stream", "second stream" and "third stream" are only used for distinguishing the three parts of the same streams which will be sent to different places.

It should be noted that the production process of epoxyalkane includes units such as reaction, separation and refining of epoxyalkane. The present disclosure mainly relates to an epoxyalkane refining unit, and particularly relates to a purification process of an extractant therein. The invention involves with an epoxyalkane refining unit in an epoxyalkane production process, and particularly involves with an epoxyalkane refining unit adopting an extractive rectification mode.

In general, the crude epoxyalkane product and the extractant are subjected to extractive rectification in an extractive rectification column, and a column kettle liquid containing the epoxyalkane and the extractant is discharged from the rectification column, preferably discharging from the rectification column kettle and entering the separation column thereby obtaining an epoxyalkane product and an extractant, wherein a part of the extractant is returned to the separation column through a column kettle reboiler, a majority of the extractant may be determined that the extractant is directly recycled or purified (regenerated) based on the purity of the extractant or the concentration of impurities in the extractant. The diols and alcohol ethers will continuously generate and accumulate in cycles during the extractive distillation process in the presence of water and methanol. It is generally believed that the extraction capacity will decrease when the concentration of impurities in the extractant reaches 10% by weight. In order to ensure the separation effect of extractive rectification and reduce energy consumption in the separation process, the concentration of impurities in the extractant is generally controlled to be less than 2% by weight, that is, when the concentration of impurities exceeds 2% by weight, the extractant shall not be directly recycled and reused, but subjecting to the purification treatment. As for the general industrial installations at present, the extractants are replenished in batches for about 2-3 years.

The inventors of the present disclosure have discovered that due to an addition of a small extractant purifier, a part of the extractant is purified and returned to the separation column, thereby improving purity of the circulating extractant and reducing loss of the extractant and the energy consumption of the separation process. The extractant purifier may be a distillation column or a reboiler. Preferably, the extractant purifier is a reboiler, and further preferably a kettle-type reboiler. The purified extractant may return to the separation column without requiring a further power device such as a power pump, such that the economic efficiency is significantly improved.

The preferred embodiment of the present disclosure is to additionally arrange one or more small reboiler at the bottom of a conventional separation column provided with a reboiler, that is, two or more reboilers are disposed in the kettle part of the separation column, which is suitable for the construction of a new device and for the upgrading and reconstruction of old equipment. For new device, such an arrangement can save equipment investment, reduce the loss of extractant and improve product quality; it is also particularly suitable for the upgrading and renovation of old devices, it generates obvious effects in term of minor modification, small land occupation, low investment and reduced loss of extractant.

Preferably, the extractant purifier is disposed between the lower part of an inlet of the separation column for introducing the stream containing epoxyalkane and extractant and the column kettle of the separation column. When the position is closer to the column kettle, the lower is the content of epoxyalkane, the higher is the content of the extractant and the impurities such as diols and alcohol ether, it is more beneficial to improve purity of the extractant, thus it is preferable that the extractant purifier is arranged underneath the feed position of the separation column. Preferably, the heights of the column kettle reboiler and the extractant purifier relative to the column kettle of the separation column are arranged such that the temperature difference between the column kettle reboiler and the extractant purifier is 5° C. In the present disclosure, the main function of the extractant purifier is to purify the extractant. The ideal condition resides in that there is no temperature difference between the column kettle reboiler and the extractant purifier relative to the column kettle of the separation column, however, in view of various influencing factors in the actual industrial production process, the present disclosure allows the temperature difference between the column kettle reboiler and the extractant purifier to be ≤5° C., preferably ≤3° C.

According to a particularly preferred embodiment, both the column kettle reboiler and the extractant purifier of the present disclosure are arranged at the column kettle of the separation column. Such an arrangement can significantly improve purity of the extractant, reduce loss of the extractant and increase yield of the epoxyalkane.

Preferably, the number of theoretical plates in the separation column is within a range of 15-80, when the number of theoretical plates is counted from the column top to the column kettle, the feed position of the extractant purifier is located at the zero to $4^{th}$ plates from the bottom, preferably the zero to $2^{nd}$ plates from the bottom.

Preferably, the ratio of the heat transfer area of the column kettle reboiler and the boiler serving as the extractant purifier is within a range of (2-5):1. That is, the ratio of the flow rate of material entering the column kettle reboiler to the flow rate of material entering the reboiler serving as the extractant purifier is within a range of (2-5):1.

The embodiment only needs to add one or more reboiler on the basis of the existing epoxyalkane production device, and the reboiler may be connected with the separation column through a simple pipeline, an additional power pump is not required for returning the purified extractant to the separation column, thus it is easy to rebuild, and requires small land occupation, low investment and reduced energy consumption.

The additionally arranged reboiler divides the third stream into the low-boiling components, and the high-boiling components with a boiling point higher than the extractant. The low-boiling components are mainly extractants, which are returned to the separation column for recycling in the form of vapor phase or vapor-liquid mixture; the high-boiling components with a boiling point higher than the extractant are mainly impurities such as diols and alcohol ethers, and are discharged from the system.

In order to further improve purity of the extractant in a method of the present disclosure, it is preferable that the first stream accounts for 2-20% by weight of the total amount of the column kettle stream of the separation column.

Preferably, the content of epoxyalkane in the stream which is obtained from the column top and mainly consisting of epoxyalkane is not less than 99.95% by weight, and the content of extractant is not higher than 0.05% by weight; the content of extractant in the stream which is obtained from the column kettle and mainly consisting of extractant is not less than 99% by weight, and the content of epoxyalkane is not higher than 1% by weight.

Preferably, the operating conditions of the separation column include: the temperature of the vapor phase at the column top is within a range of 60-130° C., the temperature at the column top is 30-80° C., and the pressure is 0.04-0.40 MPaG.

Preferably, the ratio of the extractant to the epoxyalkane in a stream containing epoxyalkane and extractant is (2-15):1, more preferably (3-10):1, and further preferably (5-7):1, based on the mole percent.

The column kettle reboiler is preferably any one of the group consisting of a thermosyphon reboiler, a kettle-type reboiler and a forced circulation type reboiler.

Preferably, the epoxyalkane is propylene oxide, butylene oxide or isomers of butylene oxide; more preferably, the epoxyalkane is butylene oxide; particularly preferably, the epoxyalkane is 1,2-butylene oxide.

In the present disclosure, the stream containing epoxyalkane and extractant may be derived from the extraction product stream obtained by extractive rectification of the olefin epoxidation reaction product. Preferably, the content of epoxyalkane in the stream is 5-25% by weight.

The extractants used for the purification of epoxyalkanes are well known in the art. Generally, C7-C20 straight and branched hydrocarbons and/or diols are used as the extractant. From an economic point of view, a mixture of C8 straight and branched alkanes is used as the extractant, and the C8 straight and branched alkanes may be N-octane, isooctane, and 2-methylheptane for example. From the sake of reducing cost of the extractant, it is preferable to select a mixture.

According to the present disclosure, after the stream containing epoxyalkane and extractant is rectified in the separation column, the column kettle stream of the separation column contains the extractant and heavy components. Taking butylene oxide as an example, the heavy components include 1,2-butanediol, 1-butanediol monomethyl ether, 2-butanediol monomethyl ether, dimer butylene oxide, (poly)butylene oxide, poly-1,2-butanediol ether and derivatives thereof, or mixtures thereof. Taking propylene oxide as an example, the heavy components include 1,2-propylene glycol, propylene glycol monomethyl ether, dimeric propylene oxide, (poly)propylene oxide, polypropylene glycol ether and derivatives thereof, or mixtures thereof.

It should be noted that the separation efficiency of extractive distillation is constant when the purity of the extractant is unchanged. However, the present disclosure emphasizes that during the refining process, side reactions may occur to generate impurities diol and its derivatives, and the production of the impurities is unavoidable, and the impurities will accumulate and circulate in the system. The impurities have an adverse effect on extractive rectification and reduce extraction efficiency of the extractant. If the extractant is directly discharged to the outside, when the heavy component impurities in the extractant are as low as 2%, the effluent extractant accounts for 98%, thus the loss of extractant is large; when the content of heavy component impurities is as high as 10%, the effluent extractant still accounts for 90%, the loss of extractant is slightly reduced, but the extraction efficiency of the extractant has decreased significantly, resulting in an increased solvent ratio of the extractive rectification column and an increase in energy consumption. In the present disclosure, merely by adding a small extractant purifier, the concentration of heavy components in the effluent stream (that is, the liquid-phase heavy component obtained in the extractant purifier) can be increased by 1 time or more, the amount of effluent extractant loss is reduced by more than half. By adopting the present disclosure, under the condition that the external discharge amount of the extractant is the same, the content of heavy component impurities in the circulating extractant is 50% of the direct external discharge scheme after a long period of operation. If the direct external discharge scheme is adopted, the yield of the epoxyalkane must be reduced in order to improve the product quality of the epoxyalkane, otherwise the product quality cannot be guaranteed.

The present disclosure is described in detail below with reference to the drawings, it should be noted that the protection scope of the present disclosure is not limited thereto, but being determined by the appended claims.

Figure 1:
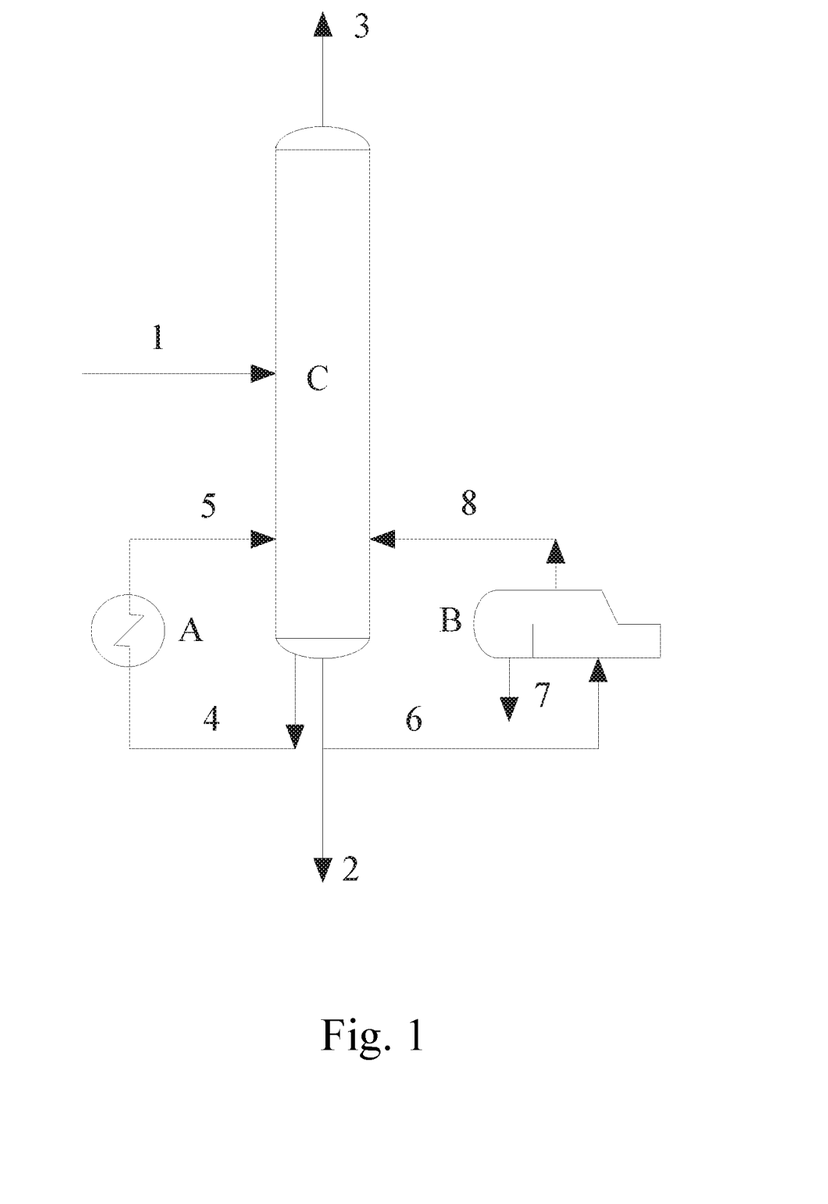
FIG. 1 is a schematic flowchart of a preferred embodiment of the method according to the present disclosure.

As illustrated in FIG. 1 of the present disclosure, the crude epoxyalkane product and the extractant are pumped to an extractive rectification column for carrying out the extractive rectification, and the raffinate is discharged from the top of the column, and the feed stream 1 containing epoxyalkane and extractant is discharged from the column kettle into the separation column C, the epoxyalkane product stream 3 is removed from the top of the separation column, the extractant stream 2 is removed from the kettle section of the separation column, the bottom of the separation column C is provided with a column kettle reboiler A and an extractant purifier B, the column kettle reboiler feed stream 4 sends a part of the column kettle stream to the column kettle reboiler A and obtain the column kettle reboiler discharge stream 5 after heating, the column kettle reboiler discharge stream 5 is recycled to the lower part of separation column C; the extractant purifier feed stream 6 sends a part of the column kettle stream to the extractant purifier B and heats it to obtain the extractant purifier discharge stream 8 as the vapor phase light component and the heavy component impurity stream-effluent stream 7 as the heavy component impurity stream, wherein the extractant purifier discharge stream 8 returns to the lower part of the separation column C, and the heavy component impurity stream-effluent stream 7 is discharged from the bottom of the extractant purifier B.

Figure 2:
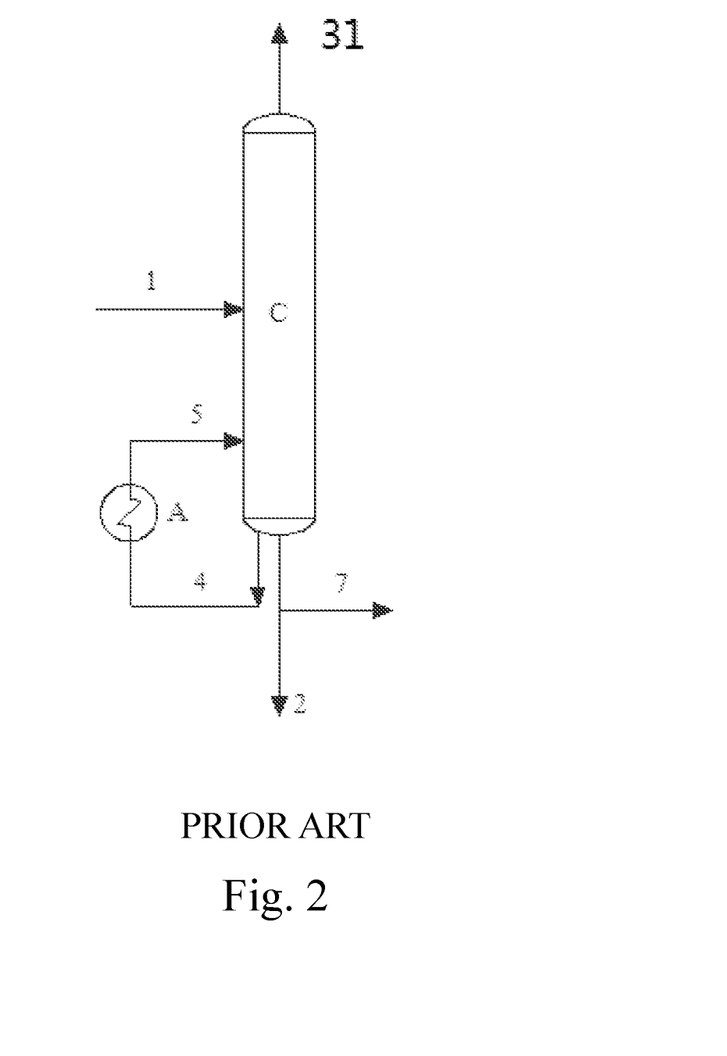
FIG. 2 is a schematic flowchart of a method provided in the prior art document U.S. Pat. No. 4,402,794.

In contrast, as illustrated in FIG. 2, the feed stream 1 containing 1,2-butylene oxide and extractant is sent to the separation column C, and the 1,2-butylene oxide product stream 31 is removed from the top of the separation column, the extractant stream 2 is removed from the kettle part of the separation column, the bottom of the separation column C is provided with a column kettle reboiler A, the column kettle reboiler feed stream 4 sends the column kettle liquid to the column kettle reboiler A and sends the column kettle reboiler discharge stream 5 obtained after heating to the lower part of the separation column C, a stream is divided from the extractant stream 2 as the heavy component impurity stream-effluent stream 7 and is discharged from the separation system. Because a part of the extractant and heavy components are discharged to reduce accumulation of the reaction by-products and derivatives in the extractant, a large amount of the extractant will be lost.

The present disclosure has no particular restrictions on the specific operating conditions for the crude product stream containing epoxyalkane and the extractant stream entering the first rectification column for performing rectification.

For example, it can be carried out with the method provided in the document CN108017598A. The content will not be repeated here.

The present disclosure will be further described below through specific examples. The results in the following examples and comparative examples are taken from the results after 800 hours of stable operation of the system. The purity of materials is measured by the Chinese national standard gas chromatography GB/T9722-2006 method. The following term "wtppm" refers to the concentration of ppm by weight.

Example 1

According to the process flow shown in FIG. 1, the operating conditions of the separation column comprise: the vapor phase temperature at the top of the column is 72° C., the temperature at the column top is 33° C., the pressure is 0.04 MPaG, and the number of theoretical plates in separation column is 65; the extractant is N-octane, the molar ratio of extractant to 1,2-butylene oxide in the feed stream containing 1,2-butylene oxide and extractant is 8:1; the column kettle reboiler A of the separation column is a thermosyphon reboiler located below the last column plate, the extractant purifier B is a kettle-type reboiler located on the $66^{th}$ column plate; the ratio of the heat transfer area of the column kettle reboiler A to that of the extractant purifier B is 5:1; the ratio of the part entering the extractant purifier relative to the column kettle stream of the separation column is 3% by weight. The temperature difference between the column kettle reboiler A and the extractant purifier B during the whole process is ≤3° C.

The 1,2-butylene oxide stream at the top of the separation column has a purity of 99.99%, a content of water ≤10 wtppm, a content of acetaldehyde+propionaldehyde ≤10 wtppm, a content of acid ≤5 wtppm and a recovery rate of 99.80%; the extractant in the kettle part of the separation column has a purity of 99.5%, the loss rate of the extractant is 0.020%.

Example 2

According to the process flow shown in FIG. 1, the operating conditions of the separation column comprise: the vapor phase temperature at the top of the column is 80° C., the temperature at the column top is 35° C., the pressure is 0.08 MPaG, and the number of theoretical plates in separation column is 60; the extractant is N-octane, the molar ratio of extractant to 1,2-butylene oxide in the feed stream containing 1,2-butylene oxide and extractant is 7:1; the column kettle reboiler A of the separation column is a thermosyphon reboiler located below the last column plate, the extractant purifier B is a kettle-type reboiler located on the $61^{st}$ column plate; the ratio of the heat transfer area of the column kettle reboiler A to that of the extractant purifier B is 5:1; the ratio of the part entering the extractant purifier relative to the column kettle stream of the separation column is 5% by weight. The temperature difference between the column kettle reboiler A and the extractant purifier B during the whole process is ≤2.4° C.

The 1,2-butylene oxide stream at the top of the separation column has a purity of 99.98%, a content of water ≤10 wtppm, a content of acetaldehyde+propionaldehyde ≤10 wtppm, a content of acid ≤5 wtppm and a recovery rate of 99.82%; the extractant in the kettle part of the separation column has a purity of 99.5%, the loss rate of the extractant is 0.025%.

Example 3

According to the process flow shown in FIG. 1, the operating conditions of the separation column comprise: the vapor phase temperature at the top of the column is 89° C., the temperature at the column top is 40° C., the pressure is 0.12 MPaG, and the number of theoretical plates in separation column is 60; the extractant is N-octane, the molar ratio of extractant to 1,2-butylene oxide in the feed stream containing 1,2-butylene oxide and extractant is 6:1; the column kettle reboiler A of the separation column is a thermosyphon reboiler located below the last column plate, the extractant purifier B is a kettle type reboiler located on the $61^{st}$ column plate; the ratio of the heat transfer area of the column kettle reboiler A to that of the extractant purifier B is 5:1; the ratio of the part entering the extractant purifier relative to the column kettle stream of the separation column is 8% by weight. The temperature difference between the column kettle reboiler A and the extractant purifier B during the whole process is ≤2° C.

The 1,2-butylene oxide stream at the top of the separation column has a purity of 99.95%, a content of water ≤10 wtppm, a content of acetaldehyde+propionaldehyde ≤10 wtppm, a content of acid ≤5 wtppm and a recovery rate of 99.85%; the extractant in the kettle part of the separation column has a purity of 99.5%, the loss rate of the extractant is 0.028%.

Example 4

According to the process flow shown in FIG. 1, the operating conditions of the separation column comprise: the vapor phase temperature at the top of the column is 96° C., the temperature at the column top is 45° C., the pressure is 0.16 MPaG, and the number of theoretical plates in separation column is 55; the extractant is N-octane, the molar ratio of extractant to 1,2-butylene oxide in the feed stream containing 1,2-butylene oxide and extractant is 5:1; the column kettle reboiler A of the separation column is a thermosyphon reboiler located below the last column plate, the extractant purifier B is a kettle-type reboiler located on the $56^{th}$ column plate; the ratio of the heat transfer area of the column kettle reboiler A to that of the extractant purifier B is 5:1; the ratio of the part entering the extractant purifier relative to the column kettle stream of the separation column is 10% by weight. The temperature difference between the column kettle reboiler A and the extractant purifier B during the whole process is ≤1.6° C.

The 1,2-butylene oxide stream at the top of the separation column has a purity of 99.95%, a content of water ≤10 wtppm, a content of acetaldehyde+propionaldehyde ≤10 wtppm, a content of acid ≤5 wtppm and a recovery rate of 99.89%; the extractant in the kettle part of the separation column has a purity of 99.5%, the loss rate of the extractant is 0.029%.

Example 5

According to the process flow shown in FIG. 1, the operating conditions of the separation column comprise: the vapor phase temperature at the top of the column is 101° C., the temperature at the column top is 50° C., the pressure is 0.20 MPaG, and the number of theoretical plates in separation column is 50; the extractant is N-octane, the molar ratio of extractant to 1,2-butylene oxide in the feed stream containing 1,2-butylene oxide and extractant is 4:1; the column kettle reboiler A of the separation column is a thermosyphon reboiler located below the last column plate, the extractant purifier B is a kettle-type reboiler located on the 51$^{st}$ column plate; the ratio of the heat transfer area of the column kettle reboiler A to that of the extractant purifier B is 5:1; the ratio of the part entering the extractant purifier relative to the column kettle stream of the separation column is 13% by weight. The temperature difference between the column kettle reboiler A and the extractant purifier B during the whole process is ≤1.2° C.

The 1,2-butylene oxide stream at the top of the separation column has a purity of 99.98%, a content of water ≤0.02%, a content of acetaldehyde+propionaldehyde ≤0.005%, a content of acid ≤0.003% and a recovery rate of 99.86%; the extractant in the kettle part of the separation column has a purity of 99.5%, the loss rate of the extractant is 0.032%.

Example 6

According to the process flow shown in FIG. 1, the operating conditions of the separation column comprise: the vapor phase temperature at the top of the column is 106° C., the temperature at the column top is 55° C., the pressure is 0.24 MPaG, and the number of theoretical plates in separation column is 45; the extractant is C8 alkane mixture, the molar ratio of extractant to 1,2-butylene oxide in the feed stream containing 1,2-butylene oxide and extractant is 4:1; the column kettle reboiler A of the separation column is a thermosyphon reboiler located below the last column plate, the extractant purifier B is a kettle-type reboiler located on the 46$^{th}$ column plate; the ratio of the heat transfer area of the column kettle reboiler A to that of the extractant purifier B is 5:1; the ratio of the part entering the extractant purifier relative to the column kettle stream of the separation column is 15% by weight. The temperature difference between the column kettle reboiler A and the extractant purifier B during the whole process is ≤1° C.

The 1,2-butylene oxide stream at the top of the separation column has a purity of 99.99%, a content of water ≤10 wtppm, a content of acetaldehyde+propionaldehyde ≤10 wtppm, a content of acid ≤5 wtppm and a recovery rate of 99.85%; the extractant in the kettle part of the separation column has a purity of 99.5%, the loss rate of the extractant is 0.035%.

Example 7

According to the process flow shown in FIG. 1, the operating conditions of the separation column comprise: the vapor phase temperature at the top of the column is 111° C., the temperature at the column top is 60° C., the pressure is 0.28 MPaG, and the number of theoretical plates in separation column is 40; the extractant is N-octane, the molar ratio of extractant to 1,2-butylene oxide in the feed stream containing 1,2-butylene oxide and extractant is 6:1; the column kettle reboiler A of the separation column is a thermosyphon reboiler located below the last column plate, the extractant purifier B is a kettle-type reboiler located on the 41$^{st}$ column plate; the ratio of the heat transfer area of the column kettle reboiler A to that of the extractant purifier B is 4:1; the ratio of the part entering the extractant purifier relative to the column kettle stream of the separation column is 7% by weight. The temperature difference between the column kettle reboiler A and the extractant purifier B during the whole process is ≤1.8° C.

The 1,2-butylene oxide stream at the top of the separation column has a purity of 99.98%, a content of water ≤10 wtppm, a content of acetaldehyde+propionaldehyde ≤10 wtppm, a content of acid ≤5 wtppm and a recovery rate of 99.85%; the extractant in the kettle part of the separation column has a purity of 99.5%, the loss rate of the extractant is 0.034%.

Example 8

According to the process flow shown in FIG. 1, the operating conditions of the separation column comprise: the vapor phase temperature at the top of the column is 111° C., the temperature at the column top is 65° C., the pressure is 0.32 MPaG, and the number of theoretical plates in separation column is 30; the extractant is N-octane, the molar ratio of extractant to 1,2-butylene oxide in the feed stream containing 1,2-butylene oxide and extractant is 6:1; the column kettle reboiler A of the separation column is a thermosyphon reboiler located below the last column plate, the extractant purifier B is a kettle-type reboiler located on the 31$^{st}$ column plate; the ratio of the heat transfer area of the column kettle reboiler A to that of the extractant purifier B is 3:1; the ratio of the part entering the extractant purifier relative to the column kettle stream of the separation column is 6% by weight. The temperature difference between the column kettle reboiler A and the extractant purifier B during the whole process is ≤1.7° C.

The 1,2-butylene oxide stream at the top of the separation column has a purity of 99.98%, a content of water ≤10 wtppm, a content of acetaldehyde+propionaldehyde ≤10 wtppm, a content of acid ≤5 wtppm and a recovery rate of 99.86%; the extractant in the kettle part of the separation column has a purity of 99.5%, the loss rate of the extractant is 0.033%.

Example 9

According to the process flow shown in FIG. 1, the operating conditions of the separation column comprise: the vapor phase temperature at the top of the column is 119° C., the temperature at the column top is 70° C., the pressure is 0.36 MPaG, and the number of theoretical plates in separation column is 25; the extractant is N-octane, the molar ratio of extractant to 1,2-butylene oxide in the feed stream containing 1,2-butylene oxide and extractant is 6:1; the column kettle reboiler A of the separation column is a thermosyphon reboiler located below the last column plate, the extractant purifier B is a kettle-type reboiler located on the 26$^{th}$ column plate; the ratio of the heat transfer area of the column kettle reboiler A to that of the extractant purifier B is 2:1; the ratio of the part entering the extractant purifier relative to the column kettle stream of the separation column is 6% by weight. The temperature difference between the column kettle reboiler A and the extractant purifier B during the whole process is ≤1.8° C.

The 1,2-butylene oxide stream at the top of the separation column has a purity of 99.95%, a content of water ≤0.02%, a content of acetaldehyde+propionaldehyde ≤0.005%, a content of acid ≤0.003% and a recovery rate of 99.87%; the extractant in the kettle part of the separation column has a purity of 99.5%, the loss rate of the extractant is 0.035%.

Example 10

The example is performed using a process similar to that of [Example 9], except that the column kettle reboiler A of this example uses a kettle-type reboiler, specifically:

According to the process flow shown in FIG. 1, the operating conditions of the separation column comprise: the vapor phase temperature at the top of the column is 119° C., the temperature at the column top is 70° C., the pressure is 0.36 MPaG, and the number of theoretical plates in separation column is 25; the extractant is N-octane, the molar ratio of extractant to 1,2-butylene oxide in the feed stream containing 1,2-butylene oxide and extractant is 6:1; the column kettle reboiler A of the separation column is a kettle-type reboiler located below the last column plate, the extractant purifier B is a kettle-type reboiler located on the 26$^{th}$ column plate; the ratio of the heat transfer area of the column kettle reboiler A to that of the extractant purifier B is 2:1; the ratio of the part entering the extractant purifier relative to the column kettle stream of the separation column is 3% by weight. The temperature difference between the column kettle reboiler A and the extractant purifier B during the whole process is ≤1.8° C.

The 1,2-butylene oxide stream at the top of the separation column has a purity of 99.95%, a content of water ≤0.02%, a content of acetaldehyde+propionaldehyde ≤0.005%, a content of acid ≤0.003% and a recovery rate of 99.87%; the extractant in the kettle part of the separation column has a purity of 99.5%, the loss rate of the extractant is 0.035%.

Example 11

The example is performed using a process similar to that of [Example 9], except that the column kettle reboiler A of this example uses a forced circulation type reboiler, specifically:

According to the process flow shown in FIG. 1, the operating conditions of the separation column comprise: the vapor phase temperature at the top of the column is 119° C., the temperature at the column top is 70° C., the pressure is 0.36 MPaG, and the number of theoretical plates in separation column is 25; the extractant is N-octane, the molar ratio of extractant to 1,2-butylene oxide in the feed stream containing 1,2-butylene oxide and extractant is 6:1; the column kettle reboiler A of the separation column is a forced circulation type reboiler located below the last column plate, the extractant purifier B is a kettle-type reboiler located on the 26$^{th}$ column plate; the ratio of the heat transfer area of the column kettle reboiler A to that of the extractant purifier B is 2:1; the ratio of the part entering the extractant purifier relative to the column kettle stream of the separation column is 6% by weight. The temperature difference between the column kettle reboiler A and the extractant purifier B during the whole process is ≤1.8° C.

The 1,2-butylene oxide stream at the top of the separation column has a purity of 99.95%, a content of water ≤0.02%, a content of acetaldehyde+propionaldehyde ≤0.005%, a content of acid ≤0.003% and a recovery rate of 99.87%; the extractant in the kettle part of the separation column has a purity of 99.5%, the loss rate of the extractant is 0.035%.

Example 12

This example is performed using a process similar to that of [Example 9], except that the column kettle reboiler A of this example uses a forced circulation type reboiler, specifically:

According to the process flow shown in FIG. 1, the operating conditions of the separation column comprise: the vapor phase temperature at the top of the column is 119° C., the temperature at the column top is 70° C., the pressure is 0.36 MPaG, and the number of theoretical plates in separation column is 26; the extractant is N-octane, the molar ratio of extractant to 1,2-butylene oxide in the feed stream containing 1,2-butylene oxide and extractant is 6:1; the column kettle reboiler A of the separation column is a forced circulation type reboiler located below the last column plate, the extractant purifier B is a kettle-type reboiler located on the 24$^{th}$ column plate; the ratio of the heat transfer area of the column kettle reboiler A to that of the extractant purifier B is 2:1; the ratio of the part entering the extractant purifier relative to the column kettle stream of the separation column is 6% by weight. The temperature difference between the column kettle reboiler A and the extractant purifier B during the whole process is ≤1.8° C.

The 1,2-butylene oxide stream at the top of the separation column has a purity of 99.95%, a content of water ≤0.02%, a content of acetaldehyde+propionaldehyde ≤0.005%, a content of acid ≤0.003% and a recovery rate of 99.85%; the extractant in the kettle part of the separation column has a purity of 99.5%, the loss rate of the extractant is 0.037%.

Comparative Example 1

According to the process flow shown in FIG. 2, the operating conditions of the separation column comprise: the temperature of vapor phase at the column top is 103° C., and the pressure is 0.22 MPaG, the number of theoretical plates in separation column is 60; the extractant is N-octane, and a ratio of the extractant and 1,2-butylene oxide is 8:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 96.38%; the extractant in the kettle part of the separation column has a purity of 99.0%, and the loss rate of the extractant is 2.02%.

When compared with the [Example 1], the separation energy consumption for purifying 1,2-butylene oxide per ton in the Comparative Example 1 is increased by 4.5%.

Comparative Example 2

According to the process flow shown in FIG. 2, the operating conditions of the separation column comprise: the temperature of vapor phase at the column top is 103° C., and the pressure is 0.22 MPaG, the number of theoretical plates in separation column is 50; the extractant is N-octane, and a ratio of the extractant and 1,2-butylene oxide is 6:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 98.50%; the extractant in the kettle part of the separation column has a purity of 99.0%, and the loss rate of the extractant is 2.20%.

Comparative Example 3

According to the process flow shown in FIG. 2, the operating conditions of the separation column comprise: the temperature of vapor phase at the column top is 103° C., and the pressure is 0.22 MPaG, the number of theoretical plates in separation column is 45; the extractant is N-octane, and a ratio of the extractant and 1,2-butylene oxide is 4:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 98.88%; the extractant in the kettle part of the separation column has a purity of 99.0%, and the loss rate of the extractant is 2.45%.

Comparative Example 4

According to the process flow shown in FIG. 2, the operating conditions of the separation column comprise: the temperature of vapor phase at the column top is 103° C., and the pressure is 0.22 MPaG, the number of theoretical plates in separation column is 40; the extractant is N-octane, and a ratio of the extractant and 1,2-butylene oxide is 3:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 97.13%; the extractant in the kettle part of the separation column has a purity of 99.0%, and the loss rate of the extractant is 2.62%.

Comparative Example 5

According to the process flow shown in FIG. 2, the operating conditions of the separation column comprise: the temperature of vapor phase at the column top is 103° C., and the pressure is 0.22 MPaG, the number of theoretical plates in separation column is 35; sending the heavy component impurity stream-effluent stream to be washed with water and then recycling the stream back so as to reduce the loss of the extractant; the extractant is N-octane, and a ratio of the extractant and 1,2-butylene oxide is 6:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 97.58%; the extractant in the kettle part of the separation column has a purity of 99.00%, and the loss rate of the extractant is 1.72%.

When compared with the [Example 1], the separation energy consumption for purifying 1,2-butylene oxide per ton in the Comparative Example 5 is increased by 6.8%.

The invention claimed is:

1. A method for producing an epoxyalkane, comprising:
1) sending a crude product stream containing an epoxyalkane and an extractant to an extractive rectification column for extractive distillation, obtaining a crude epoxyalkane stream containing the epoxyalkane and the extractant;
2) introducing the crude epoxyalkane stream into a separation column, obtaining an epoxyalkane stream from a top of the separation column and an extractant stream from a bottom of the separation column;
3) dividing the extractant stream into a first stream, a second stream, and a third stream, heating the first stream in a column reboiler connected to the separation column and returning the heated first stream to the separation column, purifying the third stream to remove heavy components having boiling points higher than that of the extractant in an extractant purifier, and obtaining a vapor phase or a vapor-liquid mixture, wherein the column reboiler is a thermosyphon reboiler, a kettle-type reboiler, and a forced circulation type reboiler; and
4) returning the vapor phase or the vapor-liquid mixture to the separation column and feeding the second stream to the extractive rectification column,
wherein the third stream accounts for 2-20% by weight of a total amount of the extractant stream,
the epoxyalkane stream contains not less than 99.95% by weight of the epoxyalkane and not higher than 0.05% by weight of the extractant, and
the extractant stream contains not less than 99% by weight of the extractant and not higher than 1% by weight of the epoxyalkane.

2. The method according to claim 1, wherein the extractant purifier is a distillation column or a second reboiler.

3. The method according to claim 2, wherein the extractant purifier is the second reboiler.

4. The method according to claim 3, wherein the second reboiler is a kettle-type reboiler.

5. The method according to claim 3, wherein the second reboiler is located at a middle part or the bottom of the separation column.

6. The method according to claim 1, wherein a temperature difference between the first stream and the third stream is ≤5° C.

7. The method according to claim 1, wherein a temperature difference between the first stream and the third stream is ≤3° C.

8. The method according to claim 1, wherein, in the separation column, a temperature of a vapor phase at the top of the separation column is within a range of 60-130° C., a pressure is 0.04-0.40 MPaG, and a number of theoretical plates is within a range of 15-80.

9. The method according to claim 1, wherein a ratio of the extractant to the epoxyalkane in a stream containing epoxyalkane and extractant is (2-15): 1, based on a mole percent.

10. The method according to claim 1, wherein a ratio of the extractant to the epoxyalkane a stream containing epoxyalkane and extractant is (3-10): 1, based on a mole percent.

11. The method according to claim 1, wherein a ratio of the extractant to the epoxyalkane a stream containing epoxyalkane and extractant is (5-7): 1, based on a mole percent.

12. The method according to claim 1, wherein the epoxyalkane is selected from propylene oxide, butylene oxide, and isomers of butylene oxide.

13. The method according to claim 1, wherein the epoxyalkane is butylene oxide.

14. The method according to claim 1, wherein the epoxyalkane is 1,2-butylene oxide.

* * * * *